(12) United States Patent
Homestad

(10) Patent No.: US 7,968,745 B2
(45) Date of Patent: *Jun. 28, 2011

(54) PURIFICATION PROCESS OF IODIXANOL

(75) Inventor: Ole Magne Homestad, Spangereid (NO)

(73) Assignee: GE Healthcare AS, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 12/097,606

(22) PCT Filed: Dec. 19, 2006

(86) PCT No.: PCT/NO2006/000487
§ 371 (c)(1),
(2), (4) Date: Jun. 16, 2008

(87) PCT Pub. No.: WO2007/073202
PCT Pub. Date: Jun. 28, 2007

(65) Prior Publication Data
US 2008/0300423 A1    Dec. 4, 2008

(30) Foreign Application Priority Data
Dec. 19, 2005   (NO) .................................. 20056041

(51) Int. Cl.
*C07C 239/00* (2006.01)

(52) U.S. Cl. ......... 564/153; 570/177; 570/178; 570/262

(58) Field of Classification Search .................. 564/153; 570/177, 178, 262
See application file for complete search history.

(56) References Cited

FOREIGN PATENT DOCUMENTS

| | | |
|---|---|---|
| EP | 0747344 | 12/1996 |
| WO | 99/18054 | 4/1999 |
| WO | WO 9918054 A1 * | 4/1999 |
| WO | 2006/016815 | 2/2006 |
| WO | WO 2006016815 A1 * | 2/2006 |
| WO | 2007/013815 | 2/2007 |

OTHER PUBLICATIONS

PCT/NO2006/000487 Int'l Search Report/Written Opinion dated Apr. 2007.

* cited by examiner

*Primary Examiner* — Sudhakar Katakam

(57) ABSTRACT

A process for the manufacture of iodixanol by performing a purification process of the crude product in a solvent comprising n-propanol. The crude product may be obtained in aqueous solution from dimerization of 5-acetamido-N,N'-bis(2,3-dihydroxypropyl)-2,4,6-triiodo-isophthalamide ("Compound A").

21 Claims, No Drawings

PURIFICATION PROCESS OF IODIXANOL

This application is a filing under 35 U.S.C. 371 of international application number PCT/NO2006/000487, filed Dec. 19, 2006, which claims priority to application number 20056041 filed Dec. 19, 2005, in Norway the entire disclosure of which is hereby incorporated by reference.

This invention is concerned with the manufacture of iodixanol (1,3-bis(acetamido)-N,N'-bis[3,5-bis(2,3-dihydroxypropylaminocarbonyl)-2,4,6-triiodophenyl]-2-hydroxypropane).

Iodixanol is the non-proprietary name of the chemical drug substance of a non-ionic X-ray contrast agent marketed under the trade name Visipaque™. Visipaque™ is one of the most used agents in diagnostic X-ray procedures and is manufactured in large quantities.

The manufacture of such non-ionic X-ray contrast agents involves the production of the chemical drug substance (referred to as primary production) followed by formulation into the drug product (referred to as secondary production). Primary production of iodixanol involves a multi step chemical synthesis and a thorough purification process. For a commercial drug product it is important for the primary production to be efficient and economical and to provide a drug substance fulfilling the specifications, e.g. as expressed on the US Pharmacopeia.

A number of methods are known for the preparation of iodixanol. These are all multi step chemical synthetic processes and the cost of the final formulated product thus mainly depends on these processes. It is therefore important to optimize the processes both for economic and environmental reasons.

Three main chemical synthetic processes are known for the preparation of iodixanol, all of which start with 5-nitroisophthalic acid. In the first process described in EP patent 108638, which document is hereby incorporated by reference, the final intermediate 5-acetamido-N,N'-bis(2,3-dihydroxypropyl)-2,4,6-triiodo-isophthalamide (hereinafter "Compound A") is reacted with a dimerisation agent such as epichlorohydrin to yield the drug substance, see Scheme I.

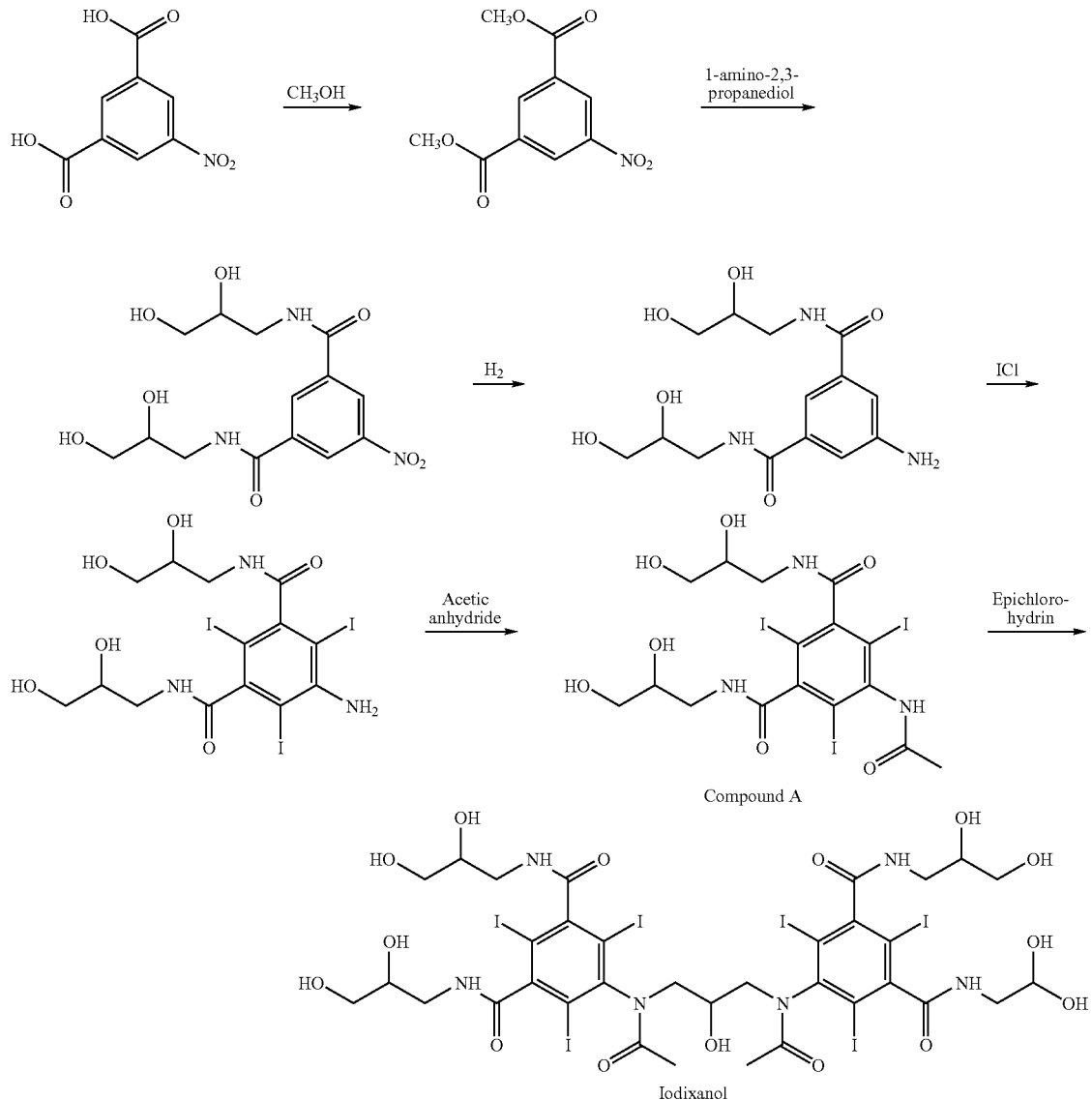

Scheme I

The overall yield in this process is relatively low and the purification of the end product iodixanol is expensive and time consuming. The purification process described in EP patent 108638 involves purification by preparative liquid chromatography. The use of preparative liquid chromatography is a serious disadvantage in industrial processes in particular due to the high costs involved.

Several attempts have been made to find alternative manufacturing processes. Attempts to increase the yield of the chemical synthesis is published by Priebe et. al. (Acta Radiol. 36 (1995), Suppl. 399, 21-31. This publication describes another route which avoids the difficult last step of the process of Scheme I. However, the route involves eight reaction steps from 5-nitroisophthalic acid, which is undesirable, and one of the steps includes chlorination with thionyl chloride, which is extremely corrosive. Also, the introduction of the iodine atoms takes place very early in the sequence, which is disadvantageous as iodine is the most expensive reagent in the process. The yield and final purification method for this route have not been reported.

The third route to iodixanol involves the synthesis of 5-amino-2,4,6-triiodoisophthalic acid (WO 96/37458) and then its dichloride (WO 96/37459), followed by conversion into Compound A (U.S. Pat. No. 5,705,692) and finally dimerisation as in the process of Scheme I. This method thus has the same disadvantages as the first process, and also uses an undesirable acid chlorination step.

Several attempts have also been made to find alternative purification procedures avoiding the liquid chromatography method described in European patent 108636.

WO 99/18054 describes a process for the crystallization of i.a. iodixanol where the crystallization is effected with high thermal energy, specifically under elevated pressure and at a temperature above the boiling point of the solution at atmospheric pressure. A number of suitable solvents are listed at page 3 of the document, including $C_{1-4}$ alcohols such as n-propanol and iso-propanol (propan-2-ol, 2-propanol). A mixture of methanol and propan-2-ol is noted as the preferred solvent according to this invention.

When iodixanol is crystallized from a mixture of methanol and 2-propanol (WO 99/18054) with a small amount of residual water under reflux, the crystallization is slow and the purification effect is limited. To achieve the desired purity, the crude iodixanol produced by the synthetic chemical process is crystallized twice. The process is time consuming and takes about 3 days for the first crystallization and about 2 days for the second one.

EP 0747344 (Hovione) describes a process for the purification of iopamidol. Iopamidol is a commercialized X-ray contrast agent sold under various trade names including Isovue™. The drug substance iopamidol is a monomeric X-ray contrast agent. In the process, iopamidol is purified by crystallization wherein propanol is added to an aqueous solution of the iopamidol and by optional azeotropic distillation to reduce the amount of water. The propanol is 1-propanol or 2-propanol. A table is provided comparing crystallization from 3 different solvents and notably the formation of a "paste" is avoided when 1-propanol and 2-propanol are used. Examples 1, 3 and 6 describe purification from 1-propanol, there is however no data provided giving e.g. the purity of the iopamidol products when treated according to the example. The amounts of the solvent 1-propanol used are quite high, from 7 to 9 ml 1-propanol/g crude iopamidol.

WO 00/27804 (Dong Kook Pharmaceutical Co., Ltd.) describes a process for the purification of iopamidol wherein anhydrous pure form of iopamidol is produced from a mixture of monohydrates, pentahydrates and anhydrous iopamidol. Iopamidol is dissolved in water, propanol or ethanol is added and the mixture is refluxed for 4 hours. The anhydrous iopamidol crystallize as white crystals. In this method, iopamidol monohydrates and pentahydrates convert into iopamidol anhydrates.

It is hence a desire to reach to a purification process where crude iodixanol as obtained by N-alkylation of Compound A as illustrated in Scheme I and hereinafter denoted "dimerisation", can be obtained in a sufficient pure form by preferably by one single crystallization step. The total crystallization time should be shortened and should not exceed 4 days. It is further desired to achieve improvements of the economy of the purification process by reducing the energy input and the amounts of solvents needed in the process and to achieve a higher output of product per unit reactor volume.

It has now surprisingly been found that using a solvent comprising n-propanol (1-propanol) in the purification step of crude iodixanol will fulfill one or more of the desired improvements listed above.

In one embodiment the present invention provides a process for the manufacture of iodixanol by performing a purification process of a crude product containing iodixanol by crystallization from a solvent comprising n-propanol in a total amount of from 2 to 5 ml per g crude product.

Further embodiments of the invention are specified in the attached claims.

Crude product is obtained from the processes known from the state of art, e.g. from the dimerisation process illustrated in Scheme I above. The dimerisation step itself may be carried out as described in European patent 108638 and WO 98/23296, for example using epichlorohydrin, 1,3-dichloro-2-hydroxypropane or 1,3-dibromo-2-hydroxypropane as the dimerisation agent. The reaction is usually carried out in a non-aqueous solvent such as a $C_{1-6}$-alcohol, preferably 2-methoxyethanol and/or methanol, and generally results in the conversion of 40 to 60% of Compound A to iodixanol. Dimerisation in pure water or mixtures of water and one or more alcohols (e.g. $C_{1-6}$-alkanols) or in a solvent comprising 1-methoxy-2-propanol is also possible. Preferably, unreacted Compound A is precipitated from the reaction mixture and recovered for reuse in a later batch as described in WO 00/47549.

Prior to the purification process step the crude product is preferably desalinated, e.g. by nanofiltration removing salt formed during the chemical synthesis, and preferably also reduction of the amount of residual starting material (Compound A) is performed e.g. by ultrafiltration. Any organic solvent used during the chemical synthesis should also be reduced if necessary to an amount not interfering substantially with the purification process.

The crude product from the dimerisation and following work-up steps is in aqueous solution with small traces of organic solvent. The crude product contains about 75-90 weight % iodixanol, 3-10 weight % iohexol, 3-7 weight % Compound A, and also minor amounts of other impurities. This crude product is the starting material for the further purification, which comprises crystallization, from a solvent comprising n-propanol. The work-up procedures are those conventionally used and known from the state of art.

In the crystallization process, the crude product comprising iodixanol in aqueous solution is adjusted to the desired water content if needed. The water removal may also be performed by distillation. After adjusting the water content to the desired level a calculated amount of n-propanol (initial amount) is added and the mixture is preferably seeded with iodixanol crystals. The water content and the amount of n-propanol depend on the desired initial supersaturation with respect to iodixanol.

The range of n-propanol/water at this initial stage should be approximately 0.5 to 8 ml of n-propanol per ml of water, preferably 1 to 6 ml of n-propanol per ml of water, more preferred 2 to 5 ml of n-propanol per ml of water, for example about 2.5 ml of n-propanol per ml of water. Further, at this stage the range of n-propanol/crude product should be approximately 0.5 to 2 ml of n-propanol per g of the crude product, preferably 0.8 to 1.5 ml of n-propanol per g of crude product, e.g. about 1.2 ml n-propanol per g of crude product.

The solution of iodixanol in the solvent mixture is heated, preferably to the boiling point and kept at the boiling point for a suitable period of time, e.g. for up to 24 hours, more suitable from 10 to 20 hours, suitably for about 16 to 20 hours. Preferably the solution is boiled with reflux for this time period which is denoted the initial crystallization step.

After the initial crystallization step, further amounts of n-propanol is added step-wise or continuously usually with increasing rate. When the water content is above the desired final level, it is reduced e.g. by azeotropic distillation. The azeotropic distillation is conducted under suitable conditions while iodixanol is precipitating from the mother liquid. The azeotropic distillation is continued until the water content is in the range of 0.1-1.0 ml/g, preferably 0.25-0.8 ml/g, and more preferably from 0.35 to 0.6 ml/g of crude product. When the desired water content is reached and the final amount of n-propanol has been added, the suspension is stirred for some time, preferably up to 30 hours and more preferred for 10 to 25 hours, to complete the crystallization. The total amount of n-propanol added is about 2 to 5 ml of n-propanol per g of the crude product, preferably 2.5 to 4.5 ml of n-propanol per g of the crude product e.g. about 3.0 to 3.6 ml n-propanol per g of crude product.

The precipitate preferably in the form of crystalline product is collected, filtered and washed, preferably with an alkanol such as n-propanol or preferably with methanol. One single purification step will usually be sufficient to obtain iodixanol in a purity satisfying the specification. The total purification process will take from 1 to 4 days, preferably 1 to 3 days and usually 2 to 3 days is adequate.

When a solvent comprising n-propanol is used in the purification process, a higher water content in the crude product can be allowed under the initiation of the crystallization process than the water content allowable when using solvents known from the state of art, e.g. solvents such as methanol/isopropanol. Iodixanol at high concentrations in water is a highly viscous solution which is difficult to handle. Higher initial water content, which is possible when using solvents comprising n-propanol, mainly avoids the problem of the handling of highly viscous solutions and also saves time and reduces energy consumption. Higher initial water content is also feasible because of the possibility of a subsequent removal of water during the crystallization.

The crystallization processes as discussed above are preferably run at a temperature of the reflux temperature of the solution. Higher temperatures promote the kinetics of the crystallization process. By using a solvent comprising n-propanol in the crystallization process it is possible to work at temperature above 80° C. at ambient pressure. The optimum working temperature depends on the water content of the solution. Even higher temperatures may be employed by increasing the pressure. When optimizing the crystallization temperature, one must also take into account that disintegration of iodixanol or its precursors (Compound A) or side products (iohexyl) may occur at high temperatures.

It has also been realized that by the use of a solvent comprising n-propanol the iodixanol crystals may be obtained in higher purity than is expected. As explained above, the purification process is finalized by filtering the precipitated iodixanol, preferably as crystals, from the solvents and finally washing the crystals with an alkanol such as n-propanol or preferably with methanol. The efficiency of the steps involving the collection, filtration and washing of the iodixanol product are dependent on the size and shape of the crystals. Surprisingly it has been found that the process of the invention gives crystals that are easier and faster to filter and to wash.

The solvent system used in the purification step will comprise water in addition to n-propanol. Optionally, further cosolvents may also be used, e.g. $C_1$ to $C_4$ alkanols such as methanol and/or ethanol.

In a still further embodiment the invention provides iodixanol as obtained by the process of the invention and where iodixanol is of a purity fulfilling the specification of the US Pharmacopeia.

The following non-limiting examples illustrate the invention.

% means weight % if not designated otherwise.

EXAMPLE 1

Crude iodixanol after nanofiltration and ultrafiltration was concentrated under reduced pressure into a solid. Water and salt content were determined and 25 g of the material, corrected for water and salt were transferred to a 200 ml Erlenmeyer flask equipped with a condenser. 0.5 ml water/g crude iodixanol (0.5 vol) were added. The material was dissolved in water under heating and stirring. After obtaining a clear solution 1.2 ml n-propanol/g crude iodixanol (1.2 vol) was added. The temperature was adjusted to reflux and 0.2 g of crystalline iodixanol was added as seeding material. Four additional portions of n-propanol were added according to the table below (addition time approx. 30 min each):

| n-proanol added, mg/l crude iodixanol | Hours after seeding |
|---|---|
| 1.5 | 0 |
| 0.3 | 19 |
| 0.4 | 26.5 |
| 0.4 | 43 |
| 1.0 | 50 |

After a total reflux time of 72 h the suspension was transferred hot to a filter and the supernatant separated. The crystals were washed with several portions of methanol and dried in vacuo.

The product was analysed by HPLC, which gave the following results: Compound A: 0.17%, iohexyl: 0.24%, iodixanol: 98.6% and other impurities: 0.92%. All these results were within specification. The yield was calculated from measurement of the UV absorbing species in the supernatant. This gave 86.3%.

What is claimed is:

1. A process for the manufacture of iodixanol by performing a purification process of a crude product containing iodixanol by crystallizing from a solvent comprising n-propanol in a total amount of from 2 to 5 ml per g crude product.

2. A process as claimed in claim 1 wherein the total amount of n-propanol is from 2.5 to 4.5 ml per g crude product.

3. A process as claimed in claim 1 wherein the total amount of n-propanol is from 3.0 to 3.6 ml per g crude product.

4. A process as claimed in claim 1 where the crude product contains about 75-90 weight % iodixanol, 3-10 weight % iohexol, 3-7 weight % Compound A and minor amounts of other impurities.

5. A process as claimed, in claim 1 where the crude product is in aqueous solution.

6. A process as claimed in claim 1 where the crystallization process comprises one or more crystallization process step.

7. A process as claimed in claim 1 where the total crystallization process time is from 1 to 4 days.

8. A process as claimed in claim 7 where the total crystallization process time is from 2 to 3 days.

9. A process as claimed in claim 1 wherein a crystallization process step comprises an initial crystallization step comprising adjusting the water content of the aqueous solution and adding the initial amount of n-propanol and optionally seeding crystals, and a heating step comprising addition of a further amount of n-propanol.

10. A process as claimed in claim 9 wherein the initial crystallization step and the heating step together forms one crystallization process step.

11. A process as claimed in claim 9 wherein in the initial crystallization step n-propanol is added to the crude product in aqueous solution in an amount of 0.5 to 2 ml per g of crude product.

12. A process as claimed in claim 11 wherein in the initial crystallization step n-propanol is added to the crude product in aqueous solution in an amount of 0.8 to 1.5 ml per g of crude product.

13. A process as claimed in claim 12 wherein in the initial crystallization step n-propanol is added to the crude product in aqueous solution in an amount of about 1.2 ml per g of crude product.

14. A process as claimed in claim 1 where the crystallization process is performed at a temperature of above 80° C.

15. A process as claimed in claim 1 where the solution from the crystallization process step is held at elevated temperature up to 30 hours.

16. A process as claimed in claim 15 where the solution from the crystallization process step is held at elevated temperature from 10 to 25 hours.

17. A process as claimed in claim 1 where the solvent comprises n-propanol, water and a cosolvent and where the cosolvent comprise $C_1$ to $C_4$ alkanols.

18. A process as claimed in claim 17 where the cosolvents comprise methanol and/or ethanol.

19. A process of claim 1 further comprising filtering and washing the precipitated iodixanol with an alkanol.

20. A process of claim 19 comprising filtering and washing the precipitated iodixanol with methanol or n-propanol.

21. A process as claimed in claim 1 where the crystallization process comprises one crystallization process step.

* * * * *